United States Patent [19]

Yamaseki et al.

[11] Patent Number: 5,510,523
[45] Date of Patent: Apr. 23, 1996

[54] PROCESS FOR THE PREPARATION OF ACETIC ACID

[75] Inventors: Kenichi Yamaseki, Mitaka; Yasuo Konishi; Hiroshi Uchida, both of Yokohama, all of Japan

[73] Assignee: Tokyo Gas Company, Limited, Tokyo, Japan

[21] Appl. No.: 901,140

[22] Filed: Jun. 19, 1992

[30] Foreign Application Priority Data

Jun. 21, 1991 [JP] Japan .................................. 3-175818

[51] Int. Cl.$^6$ ........................................... C07C 51/12
[52] U.S. Cl. ................................................. 562/519
[58] Field of Search .............................................. 562/519

[56] References Cited

U.S. PATENT DOCUMENTS

| | | | |
|---|---|---|---|
| 3,717,670 | 2/1973 | Schultz | 562/519 |
| 4,110,359 | 12/1976 | Marion | 562/519 |
| 4,111,982 | 9/1978 | Eubanks et al. | 562/579 |
| 4,994,608 | 2/1991 | Torrence et al. | 562/519 |

FOREIGN PATENT DOCUMENTS 1277242  7/1972  United Kingdom .
15018992  2/1978  United Kingdom .

OTHER PUBLICATIONS

Proceedings of the 9th International Catalysis Congress, Fujimoto et al: Effect of Hydrogen on Vapor Phase Carbonylation of Methanol, vol. 3, 1988, pp. 1051–1058.

*Primary Examiner*—Joseé G. Dees
*Assistant Examiner*—Joseph M. Conrad
*Attorney, Agent, or Firm*—Cushman Darby & Cushman

[57] ABSTRACT

A process for preparing acetic acid from methanol and carbon monoxide or a mixed gas of carbon monoxide with hydrogen, which process comprises contacting methanol with a gaseous component selected from a group consisting of carbon monoxide and a mixed gas of carbon monoxide with hydrogen of 2% by volume or less in the presence of a carbon-supported rhodium metal catalyst and methyl iodide promoter in vapor phase under the conditions of a reaction temperature of 180°–220° C., a reaction pressure of 5–10 kg/cm$^2$·G, and a weight of catalyst to feed gas flow rate ratio (W/F) of 10–20 g·h/mole; and a process for preparing acetic acid from methanol and carbon monoxide, which process comprises contacting methanol with carbon monoxide in the presence of a carbon-supported rhodium metal catalyst, methyl iodide promoter and water in vapor phase.

3 Claims, 1 Drawing Sheet

PROCESS FOR THE PREPARATION OF ACETIC ACID

BACKGROUND OF THE INVENTION

1. Field of the Invention

This invention relates to a process for preparing acetic acid from methanol and carbon monoxide or a mixed gas of carbon monoxide with hydrogen.

2. Description of the Prior Art

The so-called synthesis gas obtained by partial combustion reaction, steam reforming, etc. of coal, petroleum, natural gas, etc. has been known in the art to be used as a mixed gas of high content hydrogen with carbon monoxide which is a starting material for the preparation of acetic acid, and usually contains hydrogen in an amount of 20 to 75% by volume.

For example, Japanese Patent Publication No. 43767/85 discloses an alcohol carbonylation catalyst formed by supporting nickel, cobalt, compounds thereof and the like on a carbon support, and further discloses a process for preparing acetic acid which comprises subjecting methanol and carbon monoxide to a vapor phase catalytic reaction in the presence of the above catalyst and an iodine compound promoter, but neither teaches nor suggests the use of a mixed gas of high content hydrogen with carbon monoxide, i.e. the so-called synthesis gas as a starting material, and neither teaches nor suggests the use of a carbon-supported rhodium catalyst, resulting in unsatisfactory selectivity and yield to acetic acid.

Chemistry Letters, pp. 895–898, 1987, Fujimoto et al. reports promotion effect of hydrogen on vapor phase carbonylation of methanol over nickel on active carbon catalyst, and further reports that the yield of acetic acid reaches the maximum level at the $H_2/CO$ ratio of 0.1 or above, and shows that presence of hydrogen in such an amount as a $H_2/CO$ ratio of 0.1 or above remarkably improves the yield of acetic acid compared with the use of a hydrogen-free carbon monoxide, but with unsatisfactory results.

Proceeding of 9th International Catalysis Congress, 3, pages 1051–1058 (1988), Fujimoto et al. teaches that activity of methanol carbonylation on Rh is the highest compared with other metals such as Ni, Pd, Co and the like, and that addition of hydrogen as in the reaction conditions of 523° K., 11 atm, W/F=5 g·h/mol (Rh: 1 g·h/mol), and $CO/MeOH/MeI/H_2$=50/9/1/(19) molar ratio improves activity of carbonylation compared with the case where no hydrogen is added, showing unsatisfactory yields to acetic acid.

Japanese Patent Publication No. 3334/72 discloses a process for preparing acetic acid which comprises effecting methanol carbonylation in the liquid phase in the presence of a rhodium complex catalyst and a promoter comprising methyl iodide or hydrogen iodide to obtain acetic acid at high yields, but has such disadvantages that the reaction system is so corrosive that use of costly corrosion-resistant material is required, that by-production of methane is increased, and so forth, and neither teaches nor suggests the use of a mixed gas of high content hydrogen with carbon monoxide, i.e. the so-called synthesis gas as a starting material.

Japanese Patent Application Laid-Open No. 299248/89 discloses a process for the production from methanol of acetic acid which process comprises contacting methanol with a gaseous mixture of carbon monoxide and hydrogen in the presence of a catalyst comprising rhodium and nickel supported on a carbon support and methyl iodide promoter with unsatisfactory results such as low methanol conversion, low selectivity and yield to acetic acid, increase of the by-produced methane, and the like.

In the case of ammonia synthesis, for example, it has been known in the art that methanation of a mixed gas comprising carbon monoxide and hydrogen of 99% by volume or more may be performed at relatively low temperatures in the presence of a catalyst comprising nickel or the like.

However, methanation of a mixed gas comprising high content carbon monoxide and low content hydrogen by use of a conventionally used catalyst comprising nickel or the like results in raising such problems that decomposition of carbon monoxide results in deposition of carbon, reduction in yield of carbon monoxide, deterioration of the catalyst and in blocking in the reactor, that the use of nickel catalyst results in formation of nickel carbonyl followed by sublimation of the nickel carbonyl, and that strong adsorption of carbon monoxide onto the surface of the catalyst results in hindering the reaction.

SUMMARY OF THE INVENTION

It is an object of the present invention to provide a process for preparing acetic acid from methanol and carbon monoxide or a mixed gas of carbon monoxide with hydrogen, which process is capable of preparing acetic acid at high selectivity and yield with markedly reduced corrosion in the reaction system and markedly reduced by-produced methane according to a simplified preparation process.

A first aspect of the present invention provides a process for preparing acetic acid from methanol and carbon monoxide or a mixed gas of carbon monoxide with hydrogen, which process comprises contacting methanol with a gaseous component selected from a group consisting of carbon monoxide and a mixed gas of carbon monoxide with hydrogen of 2% by volume or less, preferably 1% by volume or less in the presence of a carbon-supported rhodium metal catalyst and methyl iodide promoter in vapor phase under the conditions of a reaction temperature of 180°–220° C., a reaction pressure of 5–10 kg/cm$^2$·G, and a weight of catalyst to feed gas flow rate ratio (W/F) of 10–20 g·h/mole.

A second aspect of the present invention provides a process for preparing acetic acid from methanol and carbon monoxide, which process comprises contacting methanol with carbon monoxide in the presence of a carbon-supported rhodium metal catalyst, methyl iodide promoter and water in vapor phase under the conditions of a reaction temperature of 150° to 300° C., a reaction pressure of 0 to 100 kg/cm$^2$·G and a weight of catalyst to feed gas flow rate ratio (W/F) of 1–30 g·h/mole.

DETAILED DESCRIPTION OF THE INVENTION

Figure 1:
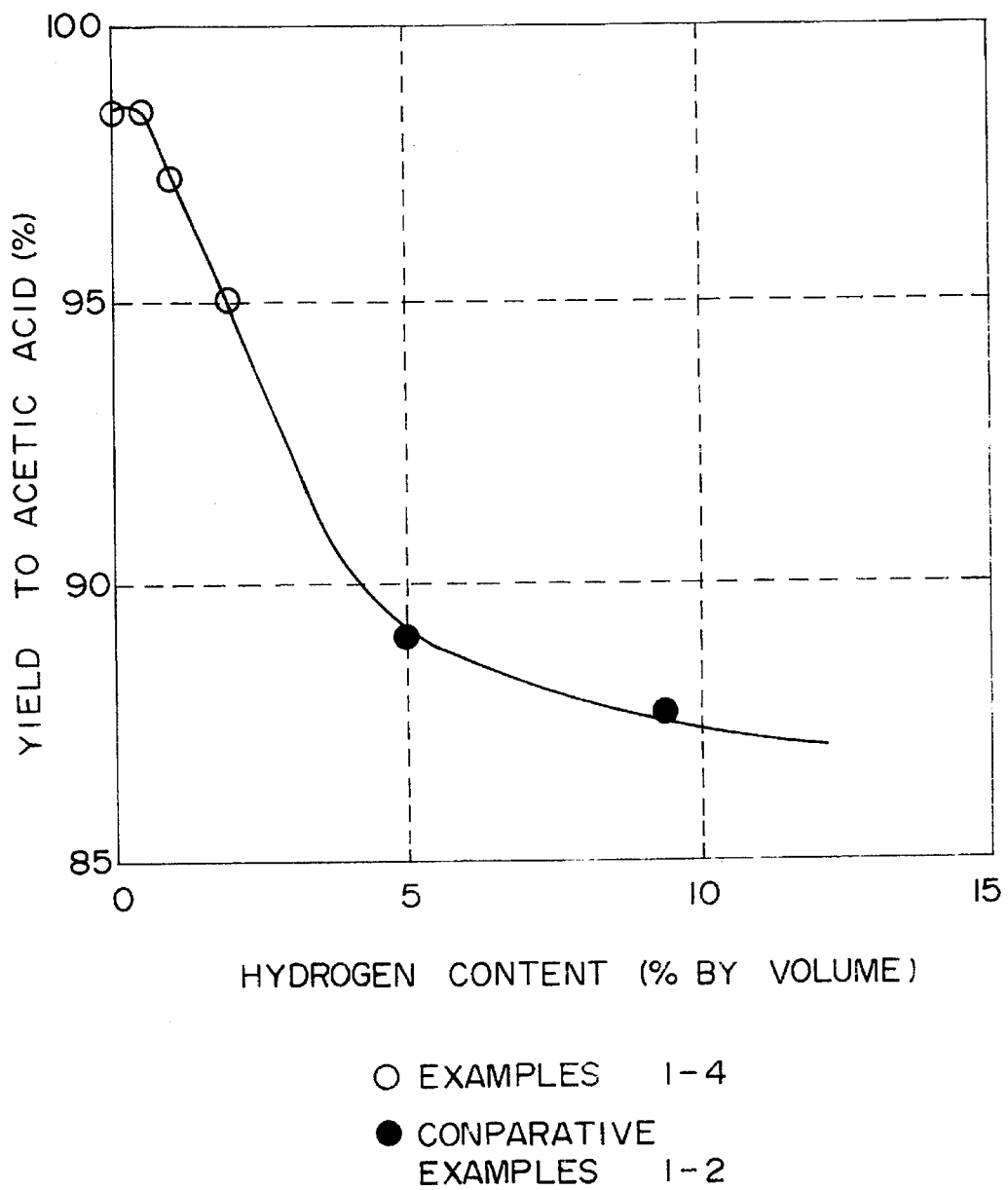
FIG. 1 is a graph showing relationship between yields to acetic acid and hydrogen contents in Examples 1–4 and Comparative Examples 1–2.

Examples of the mixed gas of carbon monoxide with high content hydrogen used in an embodiment of the present invention may include the so-called synthesis gas obtained by partial combustion, steam reforming, etc. of coal, petroleum and natural gas and containing 20 to 75% by volume of hydrogen, a mixed gas obtained by reducing carbon dioxide under hydrogen and containing 5 to 75% by volume of hydrogen, and the like.

Examples of the process for preparing the gaseous component containing 2% by volume or less, preferably 1% by volume of hydrogen may include known processes such as cuprammonium process, COSORB process, deep freeze separation process, adsorption process to utilize a selective carbon monoxide-adsorbing power of an adsorbant prepared by covering activated alumina with carbon followed by supporting CuCl and $CuCl_2$, i.e. the pressure swing adsorption process and the like, and preferably may include the following methanation process and combinations of the methanation process with the above known processes.

The above methanation process comprises introducing the above mixed gas of carbon monoxide with high content hydrogen into a reactor filled with a catalyst prepared by supporting a metal belonging to platinum group, preferably platinum on a heat-resistant support, preferably γ-alumina for carrying out a catalytic methanation reaction to remove hydrogen in the mixed gas.

The above methanation process is essentially different from the conventional methanation process for removing small amount of carbon monoxide and carbon dioxide by use of a nickel catalyst or the like in that the former is directed to a mixed gas containing carbon monoxide as a major component, whereas the latter is directed to a mixed gas containing hydrogen as a major component.

Examples of the carbon support used in the carbon-supported rhodium metal catalyst of the present invention may include inorganic supports such as carbon-supporting silica, alumina, zeolite, and the like, in addition to activated carbon, carbon black, coke, etc. Of these, activated carbon is preferred.

The amount of rhodium metal to be supported in the carbon-supported rhodium metal catalyst is not specifically limited, but usually in the range of 0.01 to 20% by weight, preferably 0.1 to 10% by weight, more preferably 1 to 5% by weight based on the weight of the catalyst.

The carbon-supported rhodium metal catalyst used in the process of the present invention may be prepared by a process which comprises supporting a rhodium reagent on a carbon support according to impregnation process, deposition process, immersion process, metallizing process, kneading process, etc., followed by evaporating water for drying at 50° to 200° C., preferably 80° to 120° C., and by flowing a hydrogen-containing gas through the catalyst at 100° to 700° C., preferably 200° to 400° C. for reduction under hydrogen atmosphere. Reduction for the preparation of the catalyst may also be carried out in the liquid phase by use of a combination of formalin with alkali.

Examples of the above rhodium reagent may include rhodium chloride, sodium chlororhodate, ammonium chlororhodate, rhodium hydroxide and the like. Of these, rhodium chloride is particularly preferred.

Since the reduction for the preparation of the catalyst may be carried out during the preparation of acetic acid too, the above reduction step is not always necessary.

The amount of methyl iodide used in the process of the present invention is not specifically limited, but is usually in the range of 0.1 to 50 moles, preferably 1 to 20 moles per 100 moles of methanol. Iodine compounds such as iodine, hydrogen iodide, which are capable of forming methyl iodide by reaction with methanol in the reaction system, may also be used as the promoter in place of methyl iodide.

The catalytic reaction in the second aspect of the present invention is carried out in the presence of water. The presence of water in the catalytic reaction according to the second aspect of the present invention increases selectivity to acetic acid and decreases selectivity to by-produced methane, resulting in greatly increasing a ratio between selectivity to acetic acid and selectivity to by-produced methane (hereinafter simply referred to as a selectivity ratio), increasing yield to acetic acid and in reducing unnecessary consumption of methanol.

The by-production of methane may be reduced, as the amount of water used in the catalytic reaction is increased. Preferably, the amount of water used in the catalytic reaction is in the range of from 3 to 50 mol % relative to methanol used. When the above amount is less than 3 mol %, the effect of reducing by-production of methane is unsatisfactory. On the other hand, when the above amount is more than 50 mol %, partial pressures of carbon monoxide and methanol in the reaction system are so reduced that methanol conversion and yield to acetic acid are undesirably reduced.

The catalytic reaction in the first aspect of the present invention is carried out by contacting methanol with carbon monoxide or with a mixed gas of carbon monoxide and hydrogen of 2% by volume or less, preferably 1% by volume or less in the presence of the above carbon-supported rhodium metal catalyst and methyl iodide promoter in vapor phase under conditions of a methanol to carbon monoxide molar ratio of 1:100 to 100:1, preferably 1:10 to 10:1, a reaction temperature of 100° to 400° C., preferably 150° to 300° C., more preferably 180° to 220° C., a reaction pressure of −0.9 to 300 $kg/cm^2 \cdot G$, preferably 0 to 100 $kg/cm^2 \cdot G$, more preferably 5 to 10 $kg/cm^2 \cdot G$, and a weight of catalyst to feed gas flow rate ratio (W/F) of 0.1 to 500 g·h/mole, preferably 1 to 30 g·h/mole, more preferably 10 to 20 g·h/mole.

The catalytic reaction in the second aspect of the present invention may be carried out by contacting methanol with carbon monoxide in the presence of a carbon-supported rhodium metal catalyst, a methyl iodide promoter and water in vapor phase under the conditions of a methanol to carbon monoxide molar ratio of 1:100 to 100:1, preferably 1:10 to 10:1, a reaction temperature of 100° to 400° C., preferably 150° to 300° C., a reaction pressure of −0.9 to 300 $kg/cm^2 \cdot G$, preferably 0 to 100 $kg/cm^2 \cdot G$, and a weight of the catalyst to feed gas flow rate ratio (W/F) of 0.1 to 500 g·h/mole, preferably 1 to 30 g·h/mole.

The catalytic action in the above catalytic reaction is not hindered by the presence of methane as an impurity.

When the above reaction temperature is higher than 400° C., by-production of methane is undesirably increased.

The reactor used in the catalytic reaction according to the process of the present invention may be of fixed catalyst bed type, fluidized bed type or moving bed type.

In principle, the reaction of methanol with carbon monoxide is effected so as to form methyl acetate and water at a first step, followed by reaction of the methyl acetate with water to form acetic acid and methanol, which is recirculated to be used as a starting material. If hydrogen presents under the above reaction conditions as in the first aspect of the present invention, the hydrogen reacts with methyl acetate to form acetic acid and methane, resulting in reducing yield to acetic acid. On the other hand, if hydrogen presents under the above reaction conditions, a reaction of the methyl iodide promoter with hydrogen causes decomposition of methyl iodide to take place, resulting in hindering the reaction for the preparation of acetic acid and in causing corrosion in the apparatus for the preparation of acetic acid because of the corrosive properties of decomposition products of methyl iodide, i.e. iodine and hydrogen iodide.

The present invention makes it possible to provide a process for preparing acetic acid from methanol and carbon monoxide or a mixed gas of carbon monoxide with hydrogen, which is capable of providing such advantages that unnecessary consumption of methyl iodide promoter is reduced so as not to hinder the reaction for the formation of acetic acid, that by-production of methane is so reduced that a recycle gas comprising unreacted carbon monoxide for recovery contains such a small amount of methane as to be reused as a starting material without needing methane separation process, and that acetic acid is prepared at high selectivity and high yield.

The present invention will be explained more in detail by the following Examples and Comparative Examples.

EXAMPLES 1–4

A granular activated carbon (marketed by Takeda Chemical Industries, LTD. under a trade name of Shirasagi C2C) was screened and classified into a particle size range of 20 to 42 meshes, i.e. 0.35 to 0.84 mm in particle size to be weighed by 15.21 g. Next, rhodium chloride was weighed by such an amount that 2.5% by weight of rhodium metal may be supported on the above activated carbon support and dissolved in water to form an aqueous solution of 100 cc. The activated carbon weighed as above was immersed in the above aqueous solution, followed by evaporating water on a water bath by use of a rotary evaporator, drying in a dryer at 120° C., and reducing under hydrogen atmosphere at 400° C. for 2 hours to obtain an activated carbon-supported rhodium metal catalyst to be used. A fixed catalyst bed flow type reaction apparatus comprising a device for feeding methanol and a gaseous component as a starting material, a methanol evaporator, a feed preheater, a reactor having an inner diameter of 10 mm, a cooler and an acetic acid-recovering device was used as a reaction apparatus.

A highly purified carbon monoxide having a purity of 99.95% (Example 1) and mixed gases of the highly purified carbon monoxide with hydrogen of 0.5% by volume (Example 2), 1% by volume (Example 3) and 2% by volume (Example 4) respectively were prepared.

Methanol and methyl iodide as starting materials were fed into the evaporator at a predetermined flow rate to be vaporized, and a gaseous component as a starting material at a predetermined flow rate was mixed with the vaporized methanol and methyl iodide to be heated up to 160° C. in the feed preheater, followed by introducing into the reactor filled with 6 g of the activated carbon-supported rhodium metal catalyst for carrying out a catalytic reaction under the conditions shown in Table 1, and cooling the reactor effluents to recover acetic acid according to gas-liquid separation process. The results are shown in Table 2 and FIG. 1.

COMPARATIVE EXAMPLES 1–2

The procedures of Example 1 were repeated except for the conditions shown in Table 1. The results are shown in Table 1 and FIG. 1.

COMPARATIVE EXAMPLES 3–5

The procedures of Example 1 were repeated except for the conditions shown in Table 1. The results are shown in Table 2.

EXAMPLES 5–6

The procedures of Example 1 were repeated except for the conditions shown in Table 1. The results are shown in Table 2.

TABLE 1

| | Reaction temperature (°C.) | Reaction pressure (kg/cm$^2$ · G) | W/F (g · h/mol) | H$_2$ content (vol %) | CO + H$_2$:methanol:CH$_3$I (molar ratio) |
|---|---|---|---|---|---|
| Example | | | | | |
| 1 | 200 | 9 | 15 | 0 | 100:20:1 |
| 2 | 200 | 9 | 15 | 0.5 | 100:20:1 |
| 3 | 200 | 9 | 15 | 1.0 | 100:20:1 |
| 4 | 200 | 9 | 15 | 2.0 | 100:20:1 |
| 5 | 200 | 5 | 15 | 0 | 100:20:1 |
| 6 | 200 | 9 | 10 | 0 | 100:20:1 |
| Comparative Example | | | | | |
| 1 | 200 | 9 | 15 | 5.0 | 100:20:1 |
| 2 | 200 | 9 | 15 | 9.4 | 100:20:1 |
| 3 | 150 | 9 | 5 | 0 | 100:20:1 |
| 4 | 250 | 9 | 5 | 0 | 100:20:1 |
| 5 | 200 | 9 | 5 | 0 | 100:20:1 |

TABLE 2

|  | Methanol conversion (%) | Selectivity (%) Acetic acid | Selectivity (%) Methane | Percentage of by-produced methane (%) | Yield to acetic acid (%) |
|---|---|---|---|---|---|
| Example |  |  |  |  |  |
| 1 | 99.99 | 98.69 | 0.23 | 0.23 | 98.5 |
| 2 | 99.99 | 98.72 | 0.68 | 0.68 | 98.5 |
| 3 | 99.99 | 97.69 | 1.50 | 1.50 | 97.3 |
| 4 | 99.99 | 95.92 | 2.72 | 2.69 | 95.1 |
| 5 | 99.96 | 90.50 | 0.13 | 0.13 | 90.27 |
| 6 | 99.91 | 93.27 | 0.13 | 0.13 | 93.00 |
| Comparative Example |  |  |  |  |  |
| 1 | 99.99 | 90.96 | 6.45 | 6.34 | 89.4 |
| 2 | 99.99 | 88.41 | 10.66 | 10.56 | 87.6 |
| 3 | 97.44 | 49.84 | 0.04 | 0.03 | 47.8 |
| 4 | 99.99 | 95.49 | 2.19 | 2.18 | 95.08 |
| 5 | 99.78 | 77.64 | 0.12 | 0.12 | 77.07 |

COMPARATIVE EXAMPLE 6

The procedures of Example 1 were repeated except that an activated carbon-supported nickel catalyst prepared by supporting 2.5% by weight of nickel metal by use of nickel acetate in place of rhodium chloride on the activated carbon support was used in place of the activated carbon-supported rhodium metal catalyst with the results that yield to acetic acid was as low as 9.6% and percentage of by-produced methane was 0.63% when carbon monoxide was used as the gaseous component, and that yield to acetic acid was improved to be 38.8% but lower compared with that of the activated carbon-supported rhodium metal catalyst, and percentage of by-produced methane was increased to be 3.33% when a mixed gas of carbon monoxide with hydrogen of 9.4% by volume was used as the gaseous component.

EXAMPLE 7

The procedures of Example 1 were repeated except for the conditions shown in Table 3. The results are shown in Table 4.

COMPARATIVE EXAMPLE 7

The procedures of Example 7 were repeated except for the conditions shown in Table 3. The results are shown in Table 4.

TABLE 3

|  | Reaction temperature (°C.) | Reaction pressure (kg/cm² · G) | W/F (g · h/mol) | CO:methanol:CH₃I (molar ratio) | Water/methanol (molar ratio) |
|---|---|---|---|---|---|
| Example 7 | 200 | 9 | 5 | 100:20:1 | 0.0965 |
| Comparative Example 7 | 200 | 9 | 5 | 100:20:1 | 0 |

TABLE 4

|  | Methanol conversion (%) | Selectivity (%) Acetic acid (b) | Selectivity (%) Methane (a) | Selectivity ratio (b/a) | Percentage of by-produced methane (%) | Yield to acetic acid (%) |
|---|---|---|---|---|---|---|
| Example 7 | 99.72 | 77.81 | 0.08 | 973 | 0.08 | 77.2 |
| Comparative Example 7 | 99.78 | 77.64 | 0.12 | 647 | 0.12 | 77.1 |

What is claimed is:

1. A process for preparing acetic acid from methanol and carbon monoxide, which process comprises:

contacting methanol with a gaseous component selected from a group consisting of carbon monoxide and a mixed gas of carbon monoxide with hydrogen of 1% by volume or less in the presence of a carbon-supported rhodium metal catalyst, a methyliodide promoter and water in vapor phase under conditions of a reaction temperature of 180°–220° C., a reaction pressure of 5–10 kg/cm²·G, and a weight of catalyst to feed gas flow rate ratio (W/F) of 10–20 g·h/mole.

2. A process for preparing acetic acid by contacting methanol and a carbon monoxide component in the presence of a carbon-supported rhodium catalyst, which process consists of contacting methanol with the carbon monoxide component which is a mixed gas of carbon monoxide with hydrogen of 2% by volume or less, in the presence of the carbon-supported rhodium metal catalyst and a methyl iodide promoter in the vapor phase, under the conditions of a reaction temperature of 180°–220° C., a reaction pressure of 5–10 kg/cm$_2$·G, and a weight of catalyst to feed gas flow ratio (W/F) of 10–20 g·h/mole, the mixed gas of carbon monoxide with hydrogen of 2% by volume or less being obtained by subjecting a mixed gas of carbon monoxide with high content hydrogen to a catalytic methanation reaction in the presence of a catalyst prepared by supporting a metal belonging to platinum group on a heat-resistant support, the mixed gas of carbon monoxide with high content hydrogen containing 5 to 75% by volume of hydrogen.

3. A process for preparing acetic acid by contacting methanol and a carbon monoxide component in the presence of a carbon-supported rhodium catalyst, which process consists of contacting methanol with the carbon monoxide component which is a mixed gas of carbon monoxide with hydrogen of 2% by volume or less, in the presence of the carbon-supported rhodium metal catalyst and a methyl iodide promoter in the vapor phase, under the conditions of a reaction temperature of 180°–220° C., a reaction pressure of 5–10 kg/cm$^2$·G, and a weight of catalyst to feed gas flow ratio (W/F) of 10–20 g·h/mole, the mixed gas of carbon monoxide with hydrogen of 2% by volume or less being obtained by subjecting a mixed gas of carbon monoxide with high content hydrogen to a catalytic methanation reaction in the presence of a catalyst prepared supporting a metal belonging to platinum group on a heat-resistant support, the mixed gas of carbon monoxide with high content hydrogen being a synthesis gas.

\* \* \* \* \*